United States Patent [19]

Dombek et al.

[11] 4,429,057

[45] Jan. 31, 1984

[54] PROCESS FOR RECOVERING VOLATILE PRECIOUS METALS

[75] Inventors: Bernard D. Dombek; George L. O'Connor, both of Charleston, W. Va.

[73] Assignee: Union Carbide Corporation, Danbury, Conn.

[21] Appl. No.: 412,033

[22] Filed: Aug. 26, 1982

Related U.S. Application Data

[63] Continuation of Ser. No. 191,246, Sep. 26, 1980.

[51] Int. Cl.³ .............................................. C07C 27/06
[52] U.S. Cl. ................................... 518/710; 518/700; 518/725; 568/902; 562/519
[58] Field of Search ................... 518/725, 700, 710; 568/902; 55/72; 423/210; 252/414

[56] References Cited

U.S. PATENT DOCUMENTS

| | | | |
|---|---|---|---|
| 2,636,046 | 4/1953 | Greshan | 515/715 |
| 3,904,547 | 9/1975 | Aycock | 560/263 |
| 4,133,966 | 1/1979 | Pretzer et al. | 568/671 |

Primary Examiner—Howard T. Mars
Attorney, Agent, or Firm—Norman L. Balmer

[57] ABSTRACT

A homogeneous catalytic process wherein a gaseous or vaporized reactant stream is continuously introduced into a liquid phase mixture containing (a) a volatile precious metal catalyst, and (b) methanol and/or ethanol as reactant or reaction product, at least a portion of the volatile precious metal being continuously removed from the liquid phase mixture by the effluent gas and/or vapor stream, and such effluent stream is an integral component of a cyclic process stream and/or a vent stream discharged from the process. The improvement is concerned with recovery of the volatilized precious metal and returning it to the liquid phase mixture which comprises passing one or both of said cyclic or vent streams through a liquid body of alcohol selected from the group consisting of methanol, ethanol and mixtures thereof at a temperature sufficiently low to effect the removal of at least a portion of the precious metal contained in said stream, and thereafter periodically or continuously introducing to the liquid phase mixture at least a portion of said liquid body containing the recovered precious metal.

3 Claims, 1 Drawing Figure

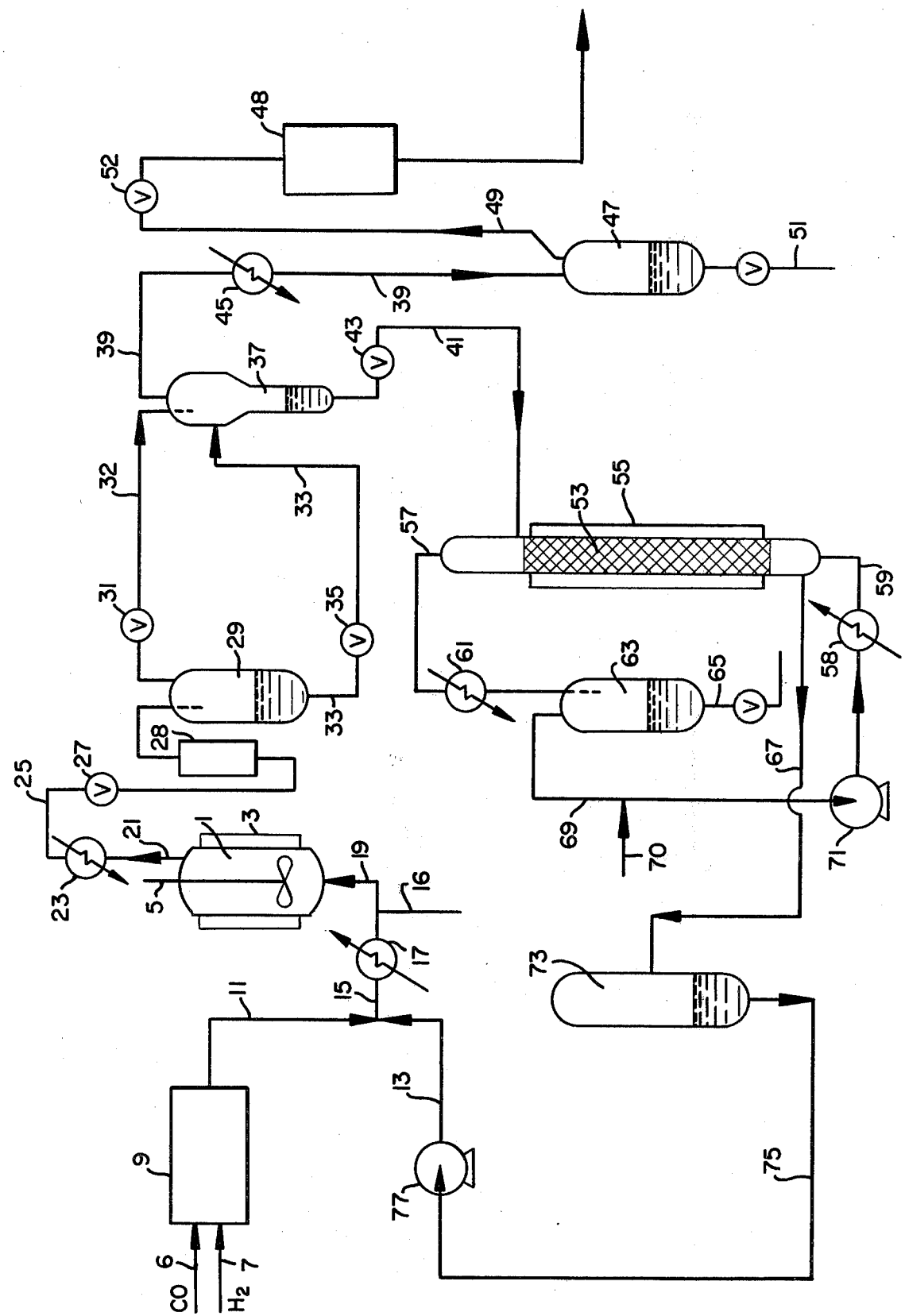

PROCESS FOR RECOVERING VOLATILE PRECIOUS METALS

This application is a Continuation of our prior U.S. application Ser. No. 191,246, filing date 9/26/1980.

This invention involves a process for the recovery of volatile precious metals derived from homogeneous catalytic reactions in which the precious metal is a component of the reaction system. In particular, the process of this invention involves the recovery of such precious metals which are contained in a gas or vapor stream in a manner such that the process can be effectively utilized in a conventional cyclic homogeneous catalytic process where methanol or ethanol is either a reactant or a reaction product.

There are many catalytic processes described in the patent literature which utilize precious metals as part of the catalytic component and in which methanol or ethanol is either a reactant or product of reaction. For example, there is described in copending U.S. patent application Ser. No. 091,242, filed Nov. 15, 1979, a process for the manufacture of methanol, ethanol and ethylene glycol by the reaction of hydrogen and carbon monoxide in a homogeneous catalytic liquid phase medium in which the catalyst comprises a soluble ruthenium carbonyl complex. There is described in U.S. Pat. No. 3,833,634, patented Sept. 3, 1974, a process for preparing glycols and methanol by reacting an oxide of carbon with hydrogen using a rhodium carbonyl complex catalyst. There is described in United Kingdom Pat. No. 1,234,641, a process for the carbonylation of methanol to produce acetic acid using solubilized noble metal catalysts selected from among compounds of iridium, platinum, palladium, osmium and ruthenium. There is described in U.S. Pat. No. 4,133,966, patented Jan. 9, 1979, a process for the homologation of methanol to produce ethanol by the reaction of synthesis gas in the presence of solubilized ruthenium and cobalt.

In all such processes, volatile precious metal compounds are capable of forming, and in a number of these processes the removal of such volatile precious metal compounds from the liquid phase reaction mixture by a gaseous effluent stream is a serious problem. Since the precious metal compounds represent a considerable cost item in the operation of such processes, it is apparent that their recovery is important to the overall economics and the operation of such processes. There is described herein a process which allows for excellent recovery of such volatile precious metals components and which allows them to be readily reintroduced to the reaction in solubilized form without modification or additional processing of any kind.

The process of this invention involves a homogeneous catalytic process wherein (a) methanol or ethanol is either a reactant or product of reaction, (b) the catalyst is a precious metal which forms volatile compounds which are removed from the reaction by a gaseous or vaporized effluent stream, and (c) such a gaseous and/or vaporized stream is an integral component of a cyclic stream of the process and/or a vent stream which is discharged from the process. The process involves the improvement which comprises passing one or both of said cyclic or vent streams containing the volatilized precious metal, through a liquid body of either methanol, ethanol or a mixture of both at a sufficiently low temperature to effect the removal by said liquid body of at least a portion of the precious metal contained in said stream. Afterwards, at least a portion of the liquid body which contains the recovered precious metal is repeatedly returned to the catalytic process and used directly therein without adverse effects. The process of the invention can thus be carried out as part of a continuous cyclic process wherein the gaseous effluent stream is continuously stripped of its precious metal content and the recovered precious metal continuously returned to the liquid phase reaction mixture. Alternatively, the liquid alcohol containing the recovered precious metal may be periodically, rather than continuously, returned to the reaction medium.

The process may be carried out in a relatively simple manner. The gas or vapor stream containing the volatile precious metal is passed through the liquid body of alcohol, desirably in such a manner that discrete treatment of the gas stream is effected and the desired degree of washing of the gas stream of the precious metal results. For example, the gas stream can be introduced through a sparger into the body of the liquid alcohol which is maintained at a temperature sufficiently low to effectively trap the precious metal therein. The sparger may conveniently be a ring having a multiplicity of orifices located at the bottom of the vessel containing the liquid alcohol. Alternatively, the sparger can be a simple tube which introduces the gas to be treated in the form of discrete bubbles at the bottom of the liquid vessel. Stirring means may be provided within the vessel to ensure good distribution of the gas through the liquid phase or there can be provided within the liquid phase inert particulate matter or a baffle-type arrangement to direct the gas flow as it travels from the bottom of the liquid body to the top so as to maximize the contact time between gas and liquid. A variety of distribution techniques can thus be employed to ensure a thorough washing of the gas by the liquid body.

The temperature of the alcohol, namely, the methanol, ethanol or mixture thereof which is employed to wash the gas stream is relatively important in the practice of the invention. The temperature of the liquid body should be sufficiently low such that when the gas is fed therethrough some portion of the precious metal contained in the gas stream is trapped in the liquid alcohol. In general, the lower the temperature of the liquid body, the more effectively it scrubs the gas stream. The temperature of the liquid body is desirably not greater than about 0° C., and preferably is maintained at a temperature below about $-10°$ C. which can be as low as 10° C. above the freezing point of the alcohol being utilized.

The material of construction of the vessel in which the gas stream is contacted with the liquid alcohol is not critical in the practice of this invention. A wide variety of materials such as glass, stainless steel, plastics, and the like can be utilized for this purpose, there being very little likelihood that at the low temperatures of the alcohol, the container will be adversely affected by the precious metal and vice-versa.

The liquid alcohol vessel can be equipped with a cooling jacket or it can be placed within a cooling medium, such as dry ice, dry ice and acetone, or a cryogenic fluid in order to effect the appropriate temperature. The extent to which the alcohol is cooled for the purpose of scrubbing the gas stream must, of course, take into consideration the strength characteristics of the vessel.

The amount of precious metal which can be present in the gas stream to be treated with liquid alcohol in accordance with the invention can range from a fractional part per million to 200 parts per million, based on the total weight of the gas stream. In most cases, such gas stream will contain precious metal in amounts ranging from about fractional parts per million to less than about 100 parts per million. The sole limitation of defining the overall effectiveness of the process of this invention resides in the capability of analyzing the gas stream when it is removed from the liquid alcohol to determine whether all of the precious metal has been removed therefrom. Thus, the process of this invention can be totally effective from the standpoint of an analytical capability whereby the removal of all of the precious metal from the stream is indicated, yet there is the possibility, in some instances, that the stream removed from the liquid body may contain very minute quantities of the precious metal.

In a preferred embodiment of the process of this invention, though such may not be necessary in order to practice the process in a commercial manner, the scrubbing action is achieved by passing the gas stream through an elongated column to which is supplied or is provided the liquid alcohol. The alcohol can thus be either continuously supplied to the top of column and thereby effect a countercurrent extraction of the precious metal from the gas stream, or alternatively, it may be more desirable from an energy standpoint to utilize a column in which the liquid alcohol is relatively stationary, but more easily cooled from the exterior or by the placement of cooling coils therein. The length of the column should be selected to achieve the desired level of extraction of the precious metal.

The particular extraction system which is utilized to effectively practice the process of this invention is not critical. The process has been very satisfactorily utilized in a glass corboy in which there is employed a particulate packing material in the liquid body. In this embodiment, the gas is supplied through a single tube containing a multiplicity of orifices at the bottom thereof and held in the bottle utilizing a conventional double-holed rubber stopper. The gas, once scrubbed, can be removed through a simple glass tube located in the remaining hole of the rubber stopper. Such a technique using methanol at $-30°$ C. is able to remove ruthenium carbonyl compounds very efficiently from a gas stream in which it is present in a concentration of less than about 100 parts per million.

An important feature of the present invention is the ability to return recovered precious metal which is contained in the liquid alcohol in a solubilized form directly to the reaction without further processing. Accordingly, the liquid alkanol is periodically or continuously, whichever is more convenient for the catalytic reaction in question, introduced into the liquid phase mixture so as to return thereto the previously volatilized precious metal catalyst. The amount of methanol and/or ethanol which is thus introduced into the liquid phase reaction medium should be regulated so as not to adversely affect the reaction kinetics and/or the selectivity of the reaction to desired products by altering the concentration of the liquid phase mixture. In general, the amount of alcohol which is introduced into the liquid phase mixture should be less than 10 weight percent of such liquid mixture.

In order to describe with particularity a continuous process in accordance with the present invention, reference is made, for purposes of illustration only, to the accompanying drawing which depicts a schematic flowsheet of a continuous operating unit for selectively producing methanol, ethylene glycol and ethanol from the reaction of hydrogen and carbon monoxide in a homogeneous catalytic process wherein a solubilized ruthenium carbonyl complex is the catalyst.

Referring to the drawing, reactor 1 is a back-mixed stirred reactor surrounded by cooling jacket 3 through which flows a heat transfer fluid for the purpose of maintaining temperature control. The temperature of reactor 1 is typically between 200° C. and 250° C. A stirrer 5 is contained within reactor 1 for the urpose of maintaining uniform distribution of product and solution in the reactor during the course of the reaction. The reactor 1 is fabricated from 316 stainless steel and is capable of withstanding pressures of up to 30,000 psi. A liquid recycle stream and synthesis gas are supplied to the reactor 1 through line 19. A carbon monoxide feed stream 6 and hydrogen stream 7 are mixed in the desired ratio using a metering system (not shown) which allows the composition of the gas to vary from pure $H_2$ to pure CO. The resultant gas feed is passed through compressor 9 to produce in line 11 a synthesis gas stream at the desired reaction pressure. This gas stream in line 11 is combined with a liquid recycle stream of solvent from line 13 and introduced via line 15 into a pre-heater 17 to heat the mixture of solvent recycle and synthesis gas in line 15 to a temperature very close to the reaction temperature utilized within reactor 1. Methanol, or ethanol is supplied to the heated feed stream through line 16 in the concentration desired for the purpose of suppressing alcohol formation. These fluid and synthesis gas feed compositions are fed into the reactor through line 19.

The effluent stream from the reactor, which is a mixture of gas and liquid containing the products of the reaction, unreacted synthesis gas, and solvent, passes through line 21 to cooler 23 where the stream temperature is reduced to about 100°–150° C. and thereafter passes through line 25 to pressure reducing valve 27 which reduces the pressure of the effluent entering hold tank 28 to about 1,500 psi. Hold tank 28 which contains stainless steel packing rings to enhance gas-liquid contact serves to resolubilize volatilized ruthenium complex compounds into the liquid stream. The effluent of tank 28 enters separator 29 wherein substantial amounts of the liquid product and solvent are separated from the effluent stream, the resultant liquid being collected at the bottom of the separator. A portion of the unconverted reactant gas dissolved in the liquid product comes out of solution at the reduced pressure of the separator 29. From the top of separator 29, through line 32, there is removed a stream of essentially gaseous material comprising some methanol and other low boiling components as well as a significant part of the synthesis gas contained in the effluent stream of line 25. The gas stream in line 32 is passed through a throttle valve 31 which controls the pressure in separator 29 and is thereafter fed to low pressure separator 37. The liquid level in the separator 29 is controlled by valve 35 in line 33. High pressure separator 29, typically, is operated at a pressure which is approximately 10% of that contained within reactor 1, whereas low pressure separator 37 is operated at about atmospheric pressure or somewhat above atmospheric pressure. Generally, low pressure separator 37 is operated at as low a pressure as possible, taking into consideration the desire to transport the liquid streams fed therein to stripper 53.

The liquid stream which exits from the bottom of high pressure separator 29 is carried via line 33 through throttle valve 35 to low pressure separator 37, the liquid being collected at the bottom of separator 37. The gases vented from low pressure separator 37 are taken by way of line 39 into heat exchanger 45 to reduce the temperature of the stream, the condensed liquid product being collected in receiver 47. This liquid product is primarily methanol which can optionally be recycled to reactor 1 by providing a line connecting line 51 to line 16. Synthesis gas and uncondensed products are removed from receiver 47 through line 49 and pressure control valve 52, and pass through a chilled methanol scrubber 48 to recover the volatilized ruthenium compounds contained in such stream prior to being vented to the atmosphere. Typically, such vented gases are predominantly the noncondensable gases as well as very small amounts of methanol, ethanol and methyl formate.

The liquid collected in separator 37 is withdrawn through line 41 and throttle valve 43 and enters the upper portion of gas stripper 53. Stripper 53 is surrounded by steam jacket 55 and contains a stainless steel wire mesh packing of the type which creates a very low pressure drop within the column. The liquid product leaving separator 37 is stripped in stripper 53 with synthesis gas which is circulated through stripper 53 in a continuous gas recycle loop, makeup quantities of gas being provided through line 70. The synthesis gas is fed into the lower end of the stripper 53 through line 59 after having been heated in heat exchanger 58 and countercurrently strips the more volatile products contained in the liquid stream entering the stripper through line 41. Stripping gas and vapor products are removed from the overhead of the stripper 53 through line 57 and cooled in condenser 61. Stripping gas and condensed liquid products pass into receiver 63. The liquid products collected in receiver 63 are predominently methanol, ethanol and ethylene glycol, which are separated from one another by simple distillation. The stripping gas and a small amount of vapor products in receiver 63 are withdrawn through line 69 to recycle compressor 71 and are then passed to stripper 53 to complete the continuous gas loop.

The stripped liquid recovered from the bottom of stripper 53 via line 67 is carried to a collection tank 73 from which it is fed via line 75 into solvent pump 77 for recycling to reactor 1 through line 13 after being admixed with the synthesis gas in line 11 as previously described.

To further illustrate the invention, reference is made to the following example, there being no intention that such example should serve in any way to limit the scope of this invention.

EXAMPLE 1

A continuous process for the manufacture of ethylene glycol, methanol and ethanol in a homogeneous liquid phase medium containing a soluble ruthenium carbonyl catalyst was operated for a period of one month in an experimental unit such as described in the FIGURE. A detailed description of the operating conditions suitable for such process of glycol formation is set forth in co-pending U.S. application Ser. No. 190,988, filed Sept. 26, 1980.

The vent stream of the process containing synthesis gas and uncondensed products (corresponding to the stream in line 49 of the drawing) was treated in accordance with the present invention in a methanol scrubber to remove volatilized ruthenium carbonyl complexes. This gas stream which ranged in flow from about 5 to about 50 standard cubic feet per hour, was passed at atmospheric pressure through a gas dispersion tube into a 5 gallon glass carboy containing an initial charge of 8062 grams of methanol (represented in the drawing by scrubber 48). The gas dispersion tube consisted of a single Teflon (registered trademark) tube of about $\frac{3}{8}''$ inner diameter with a number of small holes at the bottom to disperse the gas in the liquid. The liquid phase also contained particulate packing (0.5" steel and ceramic rings) of the type commonly used in distillation columns, to further disperse the gas. After emerging from the liquid phase the gas was vented to the atmosphere. The liquid phase was maintained throughout most of the run at a temperature between about $-20°$ and $-30°$ C. as monitored by a thermocouple placed near the center of the container. At the end of the one-month operating period, the liquid phase weighed 13620 grams and consisted of approximately 4% water, 78% methanol, 3% acetaldehyde, 4% ethanol, and 4% 2-methyl-1,3-dioxolane. The solution also contained approximately 400 ppm of ruthenium. A further amount of ruthenium (in the form of $Ru_3(CO)_{12}$) was found adhering to the particulate packing in the liquid phase. A portion of the solution was thereafter able to be reintroduced periodically to the reactor to return the recovered ruthenium compounds to the reaction mixture without adversely affecting the reaction.

What is claimed is:

1. In a homogenous catalytic process for the production of methanol, ethylene glycol and ethanol wherein a cyclic gaseous or vaporized reactant stream comprising carbon monoxide and hydrogen is continuously introduced in a liquid phase mixture comprising (a) a volatile ruthenium catalyst and (b) methanol and/or ethanol, at least a portion of the volatile ruthenium catalyst being continuously removed from the liquid phase mixture by a gaseous and/or vaporized effluent stream, and such a gaseous and/or vaporized stream is an integral component of a cyclic stream of the process and/or a vent stream which is discharged from the process, the improvement for recovering the volatilized ruthenium catalyst and returning it to the liquid phase mixture which comprises passing one or both of said cyclic or vent gaseous or vaporized reactant streams through a liquid body of alcohol selected from the group consisting of methanol, ethanol and mixtures thereof at a temperature sufficiently low to effect the removal of at least a portion of the volatile ruthenium catalyst contained in said cyclic or vent gaseous or vaporized reactant stream, and thereafter periodically or continuously introducing to the liquid phase mixture at least a portion of said liquid body containing the recovered volatilized ruthenium catalyst.

2. The process of claim 1 wherein the temperature of the liquid body of alcohol is no greater than 0° C.

3. The process of claim 1 wherein said cyclic or vent stream is passed countercurrent to said liquid body of alcohol to effect removal of at least a portion of the volatilized ruthenium in such stream.

* * * * *